United States Patent [19]

Hodosh

[11] Patent Number: 5,522,726
[45] Date of Patent: Jun. 4, 1996

[54] METHOD FOR ANESTHETIZING TEETH

[76] Inventor: Milton Hodosh, 243 Elmwood Ave., Providence, R.I. 02907

[21] Appl. No.: 330,002

[22] Filed: Oct. 27, 1994

[51] Int. Cl.$^6$ .............................. A61K 6/00; A61K 6/02; A61K 6/027
[52] U.S. Cl. .................... 433/215; 424/677; 424/679; 424/49; 433/228.1; 514/817; 514/818; 106/35
[58] Field of Search .................. 433/215, 228.1; 514/817, 818; 424/677, 679

[56] References Cited

U.S. PATENT DOCUMENTS

| | | | |
|---|---|---|---|
| 3,863,006 | 1/1975 | Hodosh | 424/49 |
| 4,191,750 | 3/1980 | Hodosh | 424/127 |
| 4,343,608 | 8/1982 | Hodosh | 433/224 |
| 4,400,373 | 8/1983 | Hodosh | 424/49 |
| 4,407,675 | 10/1983 | Hodosh | 106/35 |
| 4,631,185 | 12/1986 | Kim | 424/49 |
| 4,634,589 | 1/1987 | Scheller | 424/49 |
| 4,710,372 | 12/1987 | Scheller | 424/49 |
| 4,751,072 | 6/1988 | Kim | 424/49 |
| 4,963,345 | 10/1990 | Forrest | 514/922 |
| 4,968,251 | 11/1990 | Darnell | 433/216 |
| 5,139,768 | 8/1992 | Friedman | 424/49 |
| 5,153,006 | 10/1992 | Hodosh | 424/718 |
| 5,160,737 | 11/1992 | Friedman et al. | 424/49 |
| 5,234,971 | 8/1993 | Akimoto | 106/35 |
| 5,240,697 | 8/1993 | Norfleet et al. | 424/52 |
| 5,252,577 | 10/1993 | Brever et al. | 106/35 |
| 5,352,439 | 10/1994 | Norfleet et al. | 424/52 |
| 5,356,291 | 10/1994 | Darnell | 433/216 |

FOREIGN PATENT DOCUMENTS

| | | |
|---|---|---|
| 945901 | 4/1974 | Canada . |
| 999238 | 11/1976 | Canada . |
| 95871 | 12/1983 | European Pat. Off. . |
| 2068405 | 10/1969 | France . |
| 1255132 | 9/1986 | U.S.S.R. . |
| 1811842 | 4/1993 | U.S.S.R. . |

*Primary Examiner*—Shep K. Rose
*Attorney, Agent, or Firm*—Salter & Michaelson

[57] ABSTRACT

The present invention is directed to a method for anesthetizing teeth which does not require an injection into the gum in order to anesthetize a tooth (or teeth) which requires attention. The method comprises the step of applying a composition having a high concentration of potassium to a tooth requiring caries removal or manual manipulation thereof. The composition is adapted to anesthetize the tooth so that the tooth may be drilled or manually manipulated. It has been discovered that the potassium enters the dentinal tubules and odontoblastic fibrils and penetrates the pulpal tissues of the tooth for anesthetizing the tooth without having to inject anesthetics into the gum surrounding the tooth.

10 Claims, No Drawings

METHOD FOR ANESTHETIZING TEETH

BACKGROUND AND SUMMARY OF THE INVENTION

This invention relates generally to methods for anesthetizing teeth, and more particularly to a method of anesthetizing teeth which require anesthesia by applying a potassium containing composition thereto.

In caries removal, crown and bridge preparation, and other manual manipulation of teeth (e.g., drilling, impression taking procedure, trial and fitting of crowns etc.), the dentist or clinician often requires the patient to receive an injectable local anesthetic. Many patients fear injections and are reluctant and even unwilling to receive injections. They will not allow the dentist to operate on their teeth without anesthesia, or, in extreme cases, they can avoid going to the dentist even when they experience pain from their teeth.

The present invention is directed to a method for anesthetizing teeth and does not require an injection into the gum in order to anesthetize a tooth (or teeth) which requires attention. The method comprises the step of applying a composition having a high concentration of potassium which will release from solution when applied to a tooth requiring caries removal or manual manipulation thereof. The composition is applied to anesthetize the tooth so that the tooth may be drilled or manipulated by instruments. It has been discovered that the potassium enters the dentinal tubules and odontoblastic processes and penetrates to the pulpal tissues of the tooth for anesthetizing the tooth without having to inject anesthetics.

Thus, although it has been discovered that potassium is effective for desensitizing hypersensitive teeth (U.S. Pat. No. 3,863,006), for treating canker sores (U.S. Pat. No. 4,191,750), for preserving dental pulp (U.S. Pat. No. 4,343,608 and 4,407,675), for treating gingival and periodontal tissues (U.S. Pat. No. 4,400,373) and for treating post-restoration dental pain (U.S. Pat. No. 5,153,006), it will be readily apparent that all of these other inventions involve problems entirely different from the problem of anesthetizing teeth without having to resort to injecting local anesthetics into the gum.

Accordingly, among the several objects of the present invention are the provision of an improved method for anesthetizing teeth which does not require injecting anesthetics into the gum; the provision of such a method for anesthetizing teeth in which a composition containing potassium is easily applied to a tooth or teeth requiring caries removal or other manual manipulation; the provision of such a method for anesthetizing teeth in which the anesthesia lasts approximately five to ten minutes; and the provision of such a method which is effective in anesthetizing teeth, while being cost-efficient and easy to apply.

Other objects, features and advantages of the invention shall become apparent as the description thereof proceeds.

DETAILED DESCRIPTION OF THE INVENTION

In general, human nerve cells have a low threshold of excitation. Stimuli for exciting nerve cells may be electrical, chemical, or mechanical. A stimulus creates a physicochemical disturbance or impulse which is transmitted by conduction along the nerve axon to its termination. Nerves do not transmit impulse passively (as do telephone wires) and conduction of nerve impulses, although rapid, is much slower than that of electricity. Conduction is an active self-propagating process which requires expenditure of energy by the nerve at a constant amplitude and velocity.

For more than one hundred years it has been known that there are electrical potential changes in a nerve when it conducts impulses. There is a constant potential difference between the inside and the outside of the nerve cell at rest. The magnitude of this potential in most neurons (otherwise referred to as "Resting Membrane Potential") is approximately seventy millivolts (MV) and is expressed as a negative potential (i.e., –70 MV) because the inside of the cell is negatively charged relative to the positively charged exterior of the cell. If the nerve axon is stimulated and a conducted impulse occurs, a characteristic series of potential changes is observed.

The first manifestation of the approaching impulse is a beginning depolarization of the membrane. The potential changes are small, being measured in millivolts. After an initial fifteen millivolts of depolarization of the membrane, the rate of depolarization increases. The point at which this change in rate occurs is termed the "firing level". Thereafter it rapidly reaches and overshoots the iso-potential (zero potential) line to approximately thirty-five millivolts positive. It then reverses and falls rapidly towards a resting level. When re-polarization is about seventy percent completed, the rate of re-polarization decreases approaching the resting level more slowly. The sharp rise and rapid fall is the spike potential of the nerve axon, and the slower fall at the end of the process is the after-depolarization. The whole sequence of potential changes is called the "action potential". Once the minimal intensity of stimulating current (threshold intensity which will just produce an impulse) is reached, a full fledged action potential is produced.

Further increases in the intensity of a stimulus produce no increment or other change in the action potential. The action potential fails to occur if the stimulus is subthreshold in magnitude, and it occurs with a constant amplitude and form regardless of the strength of the stimulus if the stimulus is at or above the threshold intensity. The action potential is therefore all or none. The depolarizing forces must be stronger than the re-polarizing forces in order to overwhelm the re-polarizing process (i.e., fifteen millivolts) and an action potential results. At this level of depolarization some fundamental change in the nerve leads to runaway depolarization in the membrane.

At rest, the nerve cell membrane is polarized with positive charges lined up along the outside of the membrane and negative charges along the inside of the membrane. During the action potential this polarity is abolished and for a brief period of time it is actually reversed. Positive charges from the membrane ahead of and behind the action potential flow into the area of negativity. By drawing off positive charges, this flow decreases the polarity of the membrane ahead of the action potential. Electronic depolarization initiates a local response, and when the firing level is reached a propagated response occurs which in turn electronically depolarizes the membrane in front of it. This sequence of events moves regularly along an unmyelinated nerve axon (i.e., a nerve axon lacking a myelin sheath) to its end. The self-propagating nature of the nerve impulse is due to circular current flow and successive electronic depolarization to the fire level of the membrane ahead of the axon potential. Once initiated, a mixing impulse does not depolarize the area behind it to the firing level because the area is refractory.

The action potentials produced at synaptic junctions also depend on electronic depolarization of the nerve cell membrane to the firing level. Conduction in myelinated axons depends on a similar pattern of current flow, but myelin is a relatively effective insulator, and current flow through it is negligible. Instead, depolarization in myelinated axons jumps from one node of Ranvier to the next, with the current sink at the active node serving to electronically depolarize to the firing level. The jumping of depolarization from node to node is called saltatory conduction. Myelinated axons conduct up to fifty times faster than unmyelinated axons.

The innervation of the tooth pulp includes both afferent neurons which conduct sensory impulses, and autonomic fibers which provide neurogenic modulation of the microcirculatory system and perhaps regulate dentinogenesis as well. Most of the nerves of the pulp fall into two categories: A-S fibers and C fibers. The A-S fibers are myelinated and the C fibers are unmyelinated. In addition to sensory nerves, sympathetic fibers from the cervical sympathetic ganglion appear with blood vessels. All of the fibers enter the tooth through the apical foramen. The A-S fibers are enclosed within sheath formed by the Schwann cells. The myelinated A-S fibers are grouped in bundles in the central region of the apical pulp. Most of the unmyelinated C fibers entering the pulp are located with the fiber bundles in the central region of the apical pulp and are situated toward the periphery of the pulp. Approximately eighty percent of the nerves of the pulp are C fibers. The nerves from the coronal pulp divide and send branches towards the peripheral pulp where a parietal layer of both myelinated and unmyelinated nerve axon form the plexus of Raschkow beneath the cell rich zone. The A-S fibers of the parietal layer emerge from their myelin sheaths and Schwann cell coverings to ramify into eight to ten unmyelinated branches forming a network under the dentin. Terminal axons exit their Schwann cell investiture and pass between the odontoblast with some fibers actually entering the dentinal tubules lying in close association with the odontoblastic processes.

A nerve axon can conduct in either direction. If an action potential is initiated in the middle of the axon, two impulses traveling in opposite directions are set up by electronic depolarization on either side of the current sink. In humans, impulses normally pass from synaptic junction or receptors along axons to their termination. Such conduction is called "orthodromic" and conduction in the opposite direction is called "antidromic". Synapses, unlike axons, permit conduction in one direction only.

It has been discovered that a tooth requiring caries removal or any other manual manipulation thereof, such as drilling, can be anesthetized by providing a composition having a high concentration of potassium and by applying the composition to the tooth requiring anesthetizing. The potassium containing composition is especially suited for anesthetizing the tooth so that the tooth may be drilled, for example. It has been further discovered that highly concentrated potassium ions and cations, when exposed to the dentinal tubules and odontoblastic processes, penetrate the pulpal tissues of the tooth, thereby anesthetizing the tooth without having to inject anesthetics into the gum surrounding the tooth. When applied to the tooth, potassium depolarizes the pulpal nervous tissues of the tooth thereby rendering these sensory nerves inactive and unable to repolarize for a significant time period until the potassium dissipates. This process allows no stimulus, no matter how strong, to excite the pulpal nervous tissue.

More specifically, in nerve cells, as in other tissues, sodium is actively transported out of the cell and a small amount of potassium is actively transported into the cell. Potassium diffuses back out of the cell down its concentration gradient, and sodium diffuses back into the cell; however, since the permeability of the membrane to potassium is much greater than it is to sodium at rest, the passive potassium efflux is much greater than the passive sodium influx. Since the membrane is impermeable to most of the anions in the cell, the potassium efflux is not accompanied by an equal flux of anions and the membrane is maintained in a polarized state with the outside of the membrane being positive and the inside of the membrane being negative.

A slight decrease in resting membrane potential leads to increased movement of potassium out of and chloride into the cell, thereby restoring the resting membrane potential. In the case of nerve cells, there is a unique change in the cell membrane when depolarization exceeds seven millivolts. This change is a voltage dependent increase in membrane permeability to sodium so that the closer the membrane potential is to the firing level the greater the sodium permeability. The electrical and concentration gradients for sodium are both directed inwardly. During a typical injected local response, sodium permeability is slightly increased, but potassium efflux is able to restore the potential to the resting value. When the firing level is reached, permeability is significant enough so that sodium influx further lowers membrane potential and sodium permeability is further increased.

The consequent sodium influx swamps the re-polarizing processes, and runaway depolarization results, producing the spike potential. With the increase in sodium permeability at the start of the action potential, the membrane potential approaches sixty millivolts positive. The membrane potential fails to reach this mark; primarily because the change in sodium permeability is short lived. Sodium permeability starts to return to the resting value during the rising phase of spike potential and sodium conductance is decreased during re-polarization. Additionally, the direction of the electrical gradient for Sodium is reversed during the overshoot because the membrane potential is reversed. These factors limit sodium influx and help bring about re-polarization.

Another important factor producing re-polarization of the nerve membrane is the increase in potassium permeability that accompanies sodium permeability. The change in potassium permeability starts more slowly and reaches a peak during the falling phase of the action potential. The increase in permeability decreases the barrier to potassium diffusion, and potassium consequently leaves the cell. The resulting net transfer of positive charge out of the cell serves to complete re-polarization.

The changes in sodium and potassium conductance of an ion is the reciprocal of its electrical resistance in a membrane and is a measure of membrane permeability to that ion. The ionic hypothesis as the basis of action potential is provided by the observation that decreasing the external sodium concentration decreases the size of the action potential, but has little effect on the resting membrane potential since the permeability of the membrane to sodium is very low. Conversely, increasing the external potassium in surrounding relation with respect to the nerves of the tooth, decreases the resting membrane potential. This renders the nerve unable to develop an action potential, and causes the nerve to fail to fire when stimulated.

In this way the potassium applied to the tooth anesthetizes the pulp directly in that potassium flows through the vast network of dentinal tubules. The potassium traverses the 30,000 dentinal tubules per square millimeter of dentin and flows over and through the dentinal tubules and odontoblastic fibrils to the odontoblast and into the pulp increasing the external potassium about the nerve. This interruption of neuron function is caused by the actual bathing of nerve tissue with an abundant source of potassium. This process of depolarizing lowers the membrane potentials as they would be in the absolute refractory period allowing no stimulus, no matter how strong, to excite the nerve. As the potassium bathing the nerve dissipates, the membrane threshold is again decreased as it would be after repolarization. At this point the patient may begin to feel some pain and concentrated potassium gel is applied again in order to re-anesthetize the tooth and eliminate pain caused by the drill etc.

In cavity preparation, it is important to adhere to basic principles when using a drill, i,e., minimize heat production, use copious water spray to avoid overheating the pulp, and use a light, painting or wiping motion when drilling. These techniques lessen the feeling in the tooth experienced by the patient. This is important especially as the clinician enters and passes through the enamel to reach the dentinal tubules. When the dentinal tubules are reached, the selected potassium composition is reapplied. This allows the potassium composition to enter into the exposed dentinal tubules.

The potassium composition of the subject invention may be in the form of a liquid, although for greater efficacy the composition preferably comprises a viscous liquid composition, such as a gel. Ointments, pastes and creams have also proven to be acceptable. In order to ensure the tooth is anesthetized, a liberal amount of the composition should be applied and reapplied as the cavity preparation proceeds. Preferably, the composition is applied over the tooth for a time period of greater than one minute before the dentist or clinician penetrates the dentine and begins cavity preparation and caries removal, or other manual manipulation of the tooth. It has been found that the potassium dissipates in approximately five to ten minutes from the time which it was applied to the tooth. If the dentist or clinician has failed to fully perform the procedure (e.g., cavity preparation) within such a time frame, or the patient is experiencing feeling in the tooth, an additional dose of the composition may be applied over the tooth and especially the dentine.

As previously stated, the composition comprising potassium is preferable in a viscous form such as a liquid gel, so that when applied liberally to the tooth, the composition tends to remain in place and is not washed away quickly. It has been found that a viscous liquid gel composition comprising a compound of potassium nitrate approaching saturation is especially effective in achieving the objectives of this invention. This composition comprises approximately 11.5% by weight potassium nitrate and 88.5% by weight hydroxyethylcellulose and water. Compositions comprising compounds other than potassium nitrate may also be applied; such compounds include potassium nitrate, potassium bicarbonate, potassium biphthalate, potassium bromide, potassium chromate, potassium dichromate, potassium phosphate, potassium sulfate, potassium chromium sulfate, potassium thiocyanate, potassium alum, potassium bitartrate, potassium bromate, potassium carbonate, potassium chlorate, potassium chloroglatinate, potassium hydroxide, potassium perchlorate, potassium persulfate, potassium oxalate, potassium azide, potassium bromate, potassium fluoride, potassium hydrogen sulfate, potassium iodate, or potassium sodium tartrate etc. However, it has been determined that potassium nitrate produces the best result.

The examples cited are based upon amounts of anhydrous substance soluble in 100 gms of water at 0° C. at 760 mm. Several examples of potassium compositions which have been effective in anesthetizing teeth are as follows:

EXAMPLE 1

| | |
|---|---|
| Hydroxyethylcellulose | 1.4%bywt. |
| Potassium acetate (KC$_2$H$_3$O$_2$) | 68.2%bywt. |
| Water (gel) | 30.4%bywt. |

EXAMPLE 2

| | |
|---|---|
| Hydroxyethylcellulose | 1.8%bywt. |
| Potassium nitrate (KNO$_3$) | 11.5%bywt. |
| Water (gel) | 86.7%bywt. |

EXAMPLE 3

| | |
|---|---|
| Hydroxyethylcellulose | 1.5%bywt. |
| Potassium chloride (KCl) | 21.3%bywt. |
| Water (gel) | 77.2%bywt. |

EXAMPLE 4

| | |
|---|---|
| Hydroxymethylcellulose | 1.6%bywt. |
| Potassium acetate (KC$_2$H$_3$O$_2$) | 68.0%bywt. |
| Water (paste) | 30.4%bywt. |

EXAMPLE 5

| | |
|---|---|
| Hydroxymethylcellulose | 2.0%bywt. |
| Potassium nitrate (KNO$_3$) | 11.5%bywt. |
| Water (paste) | 86.5%bywt. |

EXAMPLE 6

| | |
|---|---|
| Hydroxymethylcellulose | 1.8%bywt. |
| Potassium chloride (KCl) | 21.0%bywt. |
| Water (paste) | 77.2%bywt. |

EXAMPLE 7

| | |
|---|---|
| Hydroxyethylcellulose | 1.8%bywt. |
| Water (cream) | 30.3%bywt. |
| Titanium dioxide (TiO$_2$) | .6%bywt. |
| Potassium acetate (KC$_2$H$_3$O$_2$) | 67.3%bywt. |

It should be noted that suitable flavoring and/or coloring may be added to the foregoing examples. Examples 1–3 represent the composition in the form of a gel, examples 4–6 represent the composition in the form of a paste, and example 7 represents the composition in the form of a cream.

It has to be determined which potassium compound is superior for this purpose. It is not known whether a potassium compound which has a higher content of potassium ions (that is, a higher saturation level e.g., potassium acetate (KC$_2$H$_3$O$_2$) is superior than one that has a lower potassium ion content lower saturation level of potassium ions e.g., (KNO$_3$) potassium nitrate). The compound with the lower level of potassium saturation could more easily release potassium ions of an adequate quantity and effectively serve to more thoroughly bathe the pulp's nerves and be more effective than a compound that contains more potassium, but may not readily release its potassium.

Of the foregoing examples, potassium nitrate, potassium chloride, and potassium acetate have been found to be effective in producing direct pulpal anesthesia through the dentinal tubules route of application.

It should be noted that we have established that high concentrations of potassium ions applied to teeth for the purpose and in the manner described effectively anesthetizes teeth in order to allow operative and restorative dental procedures to be effectuated. It should be understood that potassium compounds which release potassium ions are effective in preventing the nerve from forming action potentials and to cause nerve repolarization which render the nerves incapable of conducting painful sensations.

As this invention may embody several forms without departing from the spirit or essential characteristics thereof, the present embodiment is therefore illustrative and not restrictive, since the scope of the invention is defined by the appended claims rather than by the description preceding them, and all changes that fall within the metes and bounds of the claims or that form their functional as well as conjointly cooperative equivalents, are therefore intended to be embraced by these claims.

What is claimed is:

1. In a method of anesthetizing a tooth requiring tooth preparation, caries removal or manual manipulation thereof, said method comprising the steps of injecting an anesthetic containing lidocaine and potassium chloride into the gum area surrounding said tooth, and drilling or manually manipulating said tooth requiring tooth preparation, caries removal or manual manipulation, wherein the improvement consists essentially of the step of applying a composition having a high concentration of potassium to the tooth requiring tooth preparation, caries removal or manual manipulation thereof, said composition being adapted to anesthetize the tooth so that the tooth may be drilled or manually manipulated, whereby said potassium enters the dentinal tubules and odontoblastic fibrils and penetrates the pulpal tissues of the tooth for anesthetizing the tooth without having to perform said step of injecting anesthetics into the gum surrounding the tooth.

2. The method as set forth in claim 1, said composition being in the form of a viscous liquid gel, liquid, ointment, paste or cream.

3. The method as set forth in claim 2, said composition being liberally applied over the dentine of the tooth.

4. The method as set forth in claim 1, said composition being in the form of a viscous liquid gel.

5. The method as set forth in claim 4, said composition comprising a compound selected from a group consisting of: potassium nitrate, potassium chloride, or potassium acetate, and said compound being saturated.

6. The method as set forth in claim 1, said composition being applied over the tooth for a time period of greater than one minute before caries removal or tooth manipulation.

7. The method as set forth in claim 1 further comprising the step of applying an additional dose of composition over the tooth when the patient experiences feeling in the tooth.

8. The method as set forth in claim 1, said potassium preventing depolarizing the pulpal nervous tissues of the tooth thereby rendering these sensory nerves inactive and unable to depolarize for a significant time period until the potassium dissipates.

9. The method as set forth in claim 7, said time period being between five and ten minutes.

10. The method as set forth in claim 1, the potassium containing composition comprising a compound selected from a group consisting of: potassium acetate; potassium nitrate; potassium bicarbonate; potassium biphthalate; potassium bromide; potassium chromate; potassium dichromate; potassium phosphate; potassium sulfate; potassium chromium sulfate; potassium thiocyanate; potassium alum; potassium bitartrate; potassium bromate; potassium carbonate; potassium chlorate; potassium chloroglatinate; potassium hydroxide; potassium perchlorate; potassium persulfate; potassium oxalate; potassium azide; potassium bromate; potassium fluoride; potassium hydrogen sulfate; potassium iodate; or potassium sodium tartrate.

\* \* \* \* \*